(12) United States Patent
Benisty

(10) Patent No.: US 8,767,207 B2
(45) Date of Patent: Jul. 1, 2014

(54) SYSTEM AND DEVICE FOR OPTICAL DETECTION OF PARTICLES WITH AN ARRAY FOR DECOUPLING OPTICAL INFORMATION, CORRESPONDING MANUFACTURING METHOD

(75) Inventor: Henri Benisty, Palaiseau (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 289 days.

(21) Appl. No.: 13/148,563

(22) PCT Filed: Feb. 11, 2010

(86) PCT No.: PCT/FR2010/000109
§ 371 (c)(1),
(2), (4) Date: Nov. 8, 2011

(87) PCT Pub. No.: WO2010/092255
PCT Pub. Date: Aug. 19, 2010

(65) Prior Publication Data
US 2012/0044485 A1    Feb. 23, 2012

(30) Foreign Application Priority Data
Feb. 12, 2009 (FR) .................................... 09 00633

(51) Int. Cl.
*G01N 15/02* (2006.01)

(52) U.S. Cl.
USPC ........... 356/336; 356/610; 356/614; 356/257; 356/219; 356/301

(58) Field of Classification Search
USPC .................. 356/336, 601–614, 257, 316, 219
See application file for complete search history.

(56) References Cited

U.S. PATENT DOCUMENTS

| | | | | |
|---|---|---|---|---|
| 5,491,344 | A * | 2/1996 | Kenny et al. ................ | 250/461.1 |
| 6,480,345 | B2 * | 11/2002 | Kawashima et al. ......... | 359/802 |
| 7,110,641 | B2 | 9/2006 | Benisty et al. | |
| 7,295,744 | B2 | 11/2007 | Benisty et al. | |
| 7,835,006 | B2 * | 11/2010 | Ja ................................... | 356/445 |
| 7,928,386 | B2 | 4/2011 | Frey et al. | |
| 2003/0169422 | A1 * | 9/2003 | Mukai ........................... | 356/399 |
| 2004/0252958 | A1 * | 12/2004 | Abu-Ageel ................... | 385/133 |
| 2005/0265659 | A1 * | 12/2005 | Miller ............................ | 385/43 |
| 2009/0290840 | A1 * | 11/2009 | Shvets .......................... | 385/101 |

FOREIGN PATENT DOCUMENTS

FR          2 785 045          4/2000

OTHER PUBLICATIONS

Bozhevolnyi, S. et al.; "Channel Plasmon-Polariton Guiding by Subwavelength Metal Grooves;" Physical Review Letters, XP002546661, vol. 95, No. 4, Jul. 22, 2005; pp. 046802-1-046802-4.
Shvets, G. et al.; "Guiding, Focusing, and Sensing on the Subwavelength Scale Using Metallic Wire Arrays;" Physical Review Letters, XP007906128, vol. 99, Aug. 2, 2007; pp. 053903-1-053903-4.
Dumais, P. et al.; "Microchannel-Based Refractive Index Sensors Monolithically Integrated With Silica Waveguides; Structures and Sensitivities;" IEEE Sensors Journal, IEEE Service Center, New York, NY, US, XP011215495, vol. 8, No. 5, May 1, 2008; pp. 457-464.

* cited by examiner

*Primary Examiner* — Tari Fur Chowdhury
*Assistant Examiner* — Isiaka Akanbi
(74) *Attorney, Agent, or Firm* — Harness, Dickey & Pierce, P.L.C.

(57) ABSTRACT

The present disclosure relates to a system for optical detection of particles arranged in a viewing area suitable for being illuminated by radiation with a predetermined wavelength. The system includes an optical detector, and an assembly of metal plasmonic channels arranged in a single plane of which one end is close enough to the viewing area to allow optical information to be transferred from one end to the other of the channels. The channels are arranged such that the assembly forms an array for transferring optical information around the viewing area. The value of at least one spatial characteristic of the array is respectively lower and higher than the wavelength near the ends of the channels that are respectively close to and far away from the viewing area. The system includes an optical decoupler between the ends that are far away from the viewing area and the optical detector.

42 Claims, 9 Drawing Sheets

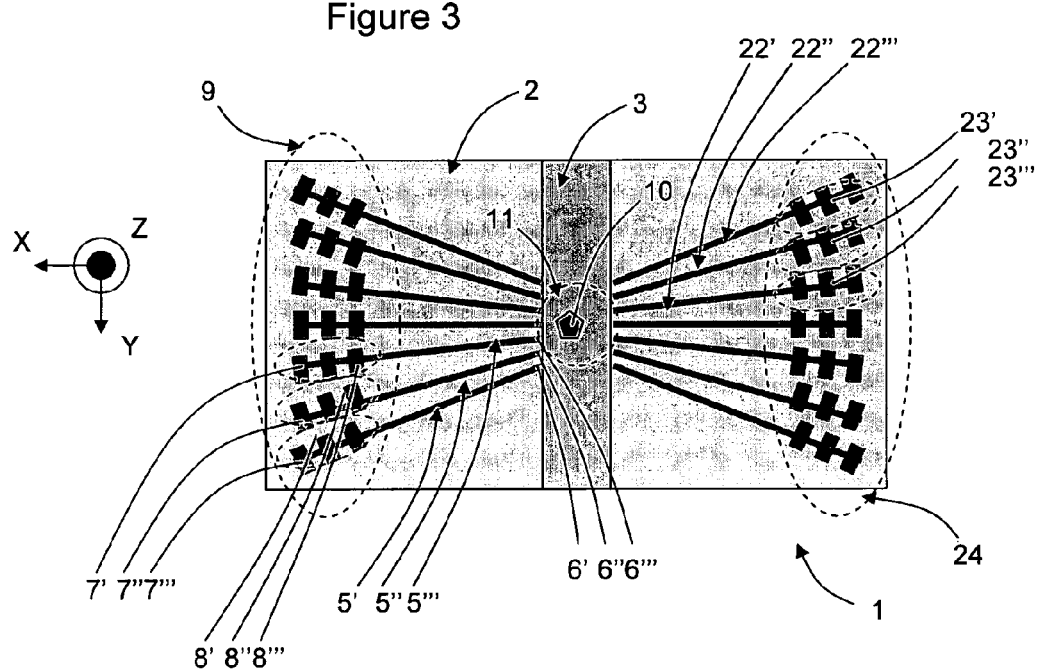
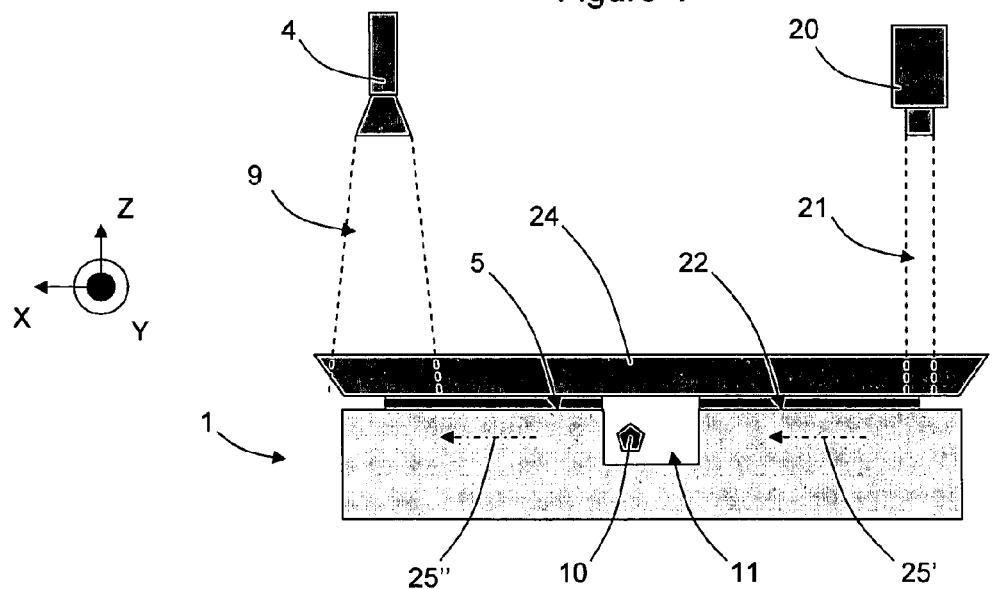

SYSTEM AND DEVICE FOR OPTICAL DETECTION OF PARTICLES WITH AN ARRAY FOR DECOUPLING OPTICAL INFORMATION, CORRESPONDING MANUFACTURING METHOD

CROSS-REFERENCE TO RELATED APPLICATIONS

This application is a National Phase Entry of International Application No. PCT/FR2010/000109, filed on Feb. 11, 2010, which claims priority to French Application Serial No. 09/00633, filed on Feb. 12, 2009, both of which are incorporated by reference herein.

TECHNICAL FIELD OF THE INVENTION

The present invention relates to the field of microscopy for optical detection of particles.

It more particularly relates to a system for optical detection of particles arranged in a viewing area suitable for being illuminated by radiation with a predetermined wavelength, said system comprises a means for optical detection, as well as an assembly of metal wires arranged in a single plane in which one end is close enough to the viewing area to allow optical information to be transferred through said metal wires.

The present invention also relates to an equipment for optical detection of particles comprising a plurality of such optical detection systems, arranged on a single substrate, as well as to manufacturing methods of such a system and of such n equipment.

PRIOR ART

In some fields such as biology or biochemistry, detecting chemically selective molecular events, such as, for example, a hybridization between proteins, between an antibody and an antigen, between streptavidin and biotin, and even between virus and membrane receptors is becoming increasingly crucial. Yet, a general problem in microscopy is the obtaining of a high resolution of the image captured by the objective, said resolution being determined by the Rayleigh criterion as inversely proportional to the numerical aperture object of the objective, but in practice limited to a maximum value in the spectrum of wave vectors which are transverse to the optical axis. Indeed, the image is obtained by applying a low-pass filter to all details existing in the plane-object, the so-called subwavelength details not being transmitted in the far field, where the objective collects the fields from the source (the plane-object) to be imaged.

To overcome this resolution restriction and to better detect nanoparticles, several solutions called "near field" microscopy or SNOM microscopy (scanning near-field optical microscopy) have been suggested, as for example in patent document FR 2 785 045 A1. According to this technique, the local part of the electromagnetic field which contains the highest spatial frequencies (near field) is coupled to the structured material. These frequencies, carrying the most spatially detailed information, cannot indeed spread to the far space and only give way to evanescent waves, undetectable after a few hundred nanometers or after a few microns at best. With this near field solution, the structured material makes it possible to convert the components of near-field into components of far field, which may then be captured. This structured material may be, for example, a thin fine metal tip or a tapered glass fiber or a glass fiber coated with a very thin metal layer.

However, this solution has a number of drawbacks relating to the problem of reproducibility of the preparation as well as of approaching the tips, of the small efficient section of the dielectric tips and, especially, of lack of parallelism. Thus, such a solution, when adapted to the research instrumentation, remains difficult to achieve industrially. The main obstacles to its realization lie in the delicacy of the manual placement of the sample and in the choice of an area to be explored, which is very small compared to the sample and both difficult and burdensome to be identified prior to local measure in a standard microscopy equipment.

A first solution to overcome these drawbacks is to optimize the existence conditions of plasmons, and in particular their cutoff frequencies. Thus, it was found that an optimal metal thickness of about 12 nanometers—this thickness may vary depending on the noble metal used—makes it possible to obtain the highest possible spatial frequency with a lossy plasmon. This type of solution is presented in publication "Planar metal plasmon waveguides: frequency-dependent dispersion, propagation, localization, and loss beyond the free electron model" (J. A. Dionne, L. A. Sweatlock, H. A. Atwater and A. Polman; Phys. Rev. B; Vol. 72; p. 075405; 2005), as well as in publication "Plasmon slot waveguides: Towards chip-scale propagation with subwavelength-scale localization" (J. A. Dionne, L. A. Sweatlock, H. A. Atwater, and A. Polman; Phys. Rev. B; Vol. 73; p. 035407; 2006) and in publication "Plasmon-polariton waves guided by thin lossy metal films of finite width: Bound modes of symmetric structures" (P. Berini; Phys. Rev. B; Vol. 61; p. 10484-10502; 2000), as well as in publication "Plasmon-polariton waves guided by thin lossy metal films of finite width: Bound modes of asymmetric structures," (P. Berini, Phys. Rev. B, Vol. 53, p. 125417, 2001). In the first two publications mentioned, it is also instructed the value of the geometry of slot waveguide. Other geometries have also been successfully proposed to form small section plasmonic metal channels, for example V-grooves as presented in publication "Channel Plasmon-Polariton Guiding by Subwavelength Metal Grooves," (S. I. Bozhevolnyi, V. S. Volkov, E. Devaux, and T. W. Ebbesen, Phys. Rev. Lett; Vol. 95; p. 046802 (1-4); 2005). These alternative solutions have less confined plasmons than those of mentioned thin wires, but may retain an interest in the applications envisaged here.

A second solution is to take advantage of the particular propagation of the evanescent waves in metal multilayers. Due to an equivalent negative index, a metal plane acts as a "superlens" capable of taking the image of a point situated under it to a point above it, with a unit-magnification and a noticeable subwavelength resolution. Different alternatives of superlens were also suggested in order to obtain an image formation with variable magnification as in conventional optics. Thus, according to a first alternative, circular slices have been suggested to form a magnifying superlens, as for example in publication "Magnifying Superlens in the Visible Frequency Range" (Igor I. Smolyaninov, Yu-Ju Hung, Christopher C. Davis; SCIENCE; Vol. 315; p. 1699-1701; Mar. 23, 2007). According to a second alternative, it was suggested to set up a metal multilayer assembly of the superlens type on a micrometric half-cylinder, the resulting curve making it possible to take the enlarged image of the area under the half-cylinder, as for example in publication "Far-Field Optical Hyperlens Magnifying Sub-Diffraction-Limited Objects" (Zhaowei Liu, Hyesog Lee, Yi Xiong, CHen Sun, Xiang Zhang; SCIENCE; Vol. 315; p. 1686; Mar. 23, 2007).

The first solution, although easier to manufacture than a SNOM tip, does not allow to obtain a subwavelength resolution, or even a "super-resolution", which is particularly restricted by metals and plasmons. The second solution provides a better optical potential, with access to the super-resolution, but is difficult to be implemented in the vicinity of a fluid duct, because the half-cylinder must be perfect and must be exactly above the most structured system area, and finally the resolution is not reached along the axis of the half-cylinder, but only across the cylinder.

Therefore, no solution of the state of the art provides a microscopy of subwavelength resolution to make it possible to improve the optical detection of the small particles, up to nanometric dimensions, while presenting characteristics which make it suitable for industrial production.

SUMMARY OF THE INVENTION

The aim of this invention is to overcome this technical problem by offering metal systems which individualize plasmonic channels, particularly discontinuous metal systems. To this end, the invention is based on a plurality of metal plasmonic channels converging towards the viewing area of the nanoparticles to be detected, these possibly flowing in a fluid.

To this end, the invention relates to a system for optical detection of particles arranged in a viewing area suitable for being illuminated by radiation with a predetermined wavelength. This system comprises a means for optical detection, and an assembly of metal plasmonic channels arranged in a single plane in which one end is close enough to the viewing area to allow optical information to be transferred from one end to the other. In this system, the channels are arranged such that the assembly forms around the viewing area an array for transferring optical information. The value of at least one spatial characteristic of the array is lower than the wavelength at the ends of the channels close to the viewing area. The value of at least one spatial characteristic of the array is higher than the wavelength at the ends of the channels far away from the viewing area. The system includes means for optical decoupling between the ends far away from the viewing area and the optical detection means.

In this patent, what is meant by metal plasmonic channel is a channel allowing the passage of the optical information in a plasmonic form. This type of channel can be achieved in various ways, particularly by metal wires or by grooves made in a metal layer.

This solution, which combines an original arrangement of metal plasmonic channels and means for decoupling optical signals, makes it possible to transcribe the magnified optical information so that it is received in the far-field by an optical detection means known in the microscopy field. Indeed, the channels shaped in array makes it possible to couple a sub-wavelength near-field area with a recovery area where the spatial characteristics of the channels are modified so as to radiate the optical information acquired locally and enlarged at the passage of the array to conventional detection means. Due to the spatial characteristics of the plasmonic channels at each one of their ends, it is possible to achieve a subwavelength microscopy resolution, making it possible to detect particles with nanometric dimensions.

Preferably, the value of at least one spatial characteristic of the channels array is lower than half the wavelength at the ends close to the viewing area.

According to a first embodiment, a spatial characteristic of the channels array is the distance between two adjacent channels.

According to a second embodiment, a spatial characteristic of the channels array is the channel width.

According to a first implementation of the invention, the metal plasmonic channels are made up of metal wires.

According to a second implementation of the invention, the metal plasmonic channels are made up of V grooves notching a metal layer.

In this last case, a spatial characteristic of the channels array may be the depth of the grooves forming the array.

Still in the case of plasmonic channels in the form of grooves, the tilt angle of the grooves is preferably steeper at the ends near the viewing area than at the far away ends.

In a preferred embodiment, the channels of the transferring array are deposited on a substrate, which makes holding the array possible. It may also be provided that the wires of the array be buried. In this case, it is possible to form a symmetrical system and then use the teachings of publication "Plasmon-polariton waves guided by thin lossy metal films of finite width: Bound modes of symmetric structures" (P. Berini; Phys. Rev. B; Vol. 61; p. 10484-10502; 2000).

In case the array wires are buried, they may be extended at the viewing area in the form of close parallel channels. In this embodiment, the distance between the bottom of the viewing area and the channels buried under this area remain subwavelength, so that the sought optical information remains accessible with a sufficient signal. This technique may allow a better geometric control of the shape than in the case of a cutoff array on the edge of the viewing area.

Preferably, a groove is provided in the substrate so as to form a channel for the flow of a fluid carrying the particles to be detected. This groove may be covered to prevent evaporation, either by a lid along the groove itself or by a whole superstrate provided on the substrate, in particular a flexible material superstrate such as elastomers, silicones, etc., as known for a man skilled in the art of micro fluidics and "lab-on-a-chip".

The invention also relates to a system for optical detection as described above in which the channels of the transfer array are buried, these channels extending under the viewing area to form a network of parallel channels, the distance between two adjacent parallel channels being lower than the wavelength of the radiation, the channels being located under the viewing area at a depth lower than the wavelength of the radiation.

When a fluid can flow along a channel, it may be provided that at the viewing area, miniature electromechanical transducers are associated with the transfer array channels or controlled by said channels for the control of the fluid flow lines or for the specific control of the particles moving in this fluid.

According to a particular embodiment, the optical decoupling means include network extractors located at the far end of the viewing area, which makes it possible to couple the plasmonic modes towards the superstrate substantially along the vertical line to the array plane.

According to a particular alternative of these networks extractors, these extractors consist of a modulation of the width of the ends of the transfer array at the scale of the wavelength.

According to another particular embodiment, the means for optical decoupling comprise network extractors located at high index dielectric wires arranged at the end of the channels far away from the viewing area and in the extension of these channels. Compared to the metal case, these extractors offer a larger propagation length, thus an open side of the array arbitrarily far away from the viewing area.

According to a particular embodiment of these network extractors, these consist of a modulation of the width or of the section of the dielectric wires.

According to another particular embodiment of these network extractors, these extractors consist of perforating holes in all or part of the central dielectric wires.

According to a first alternative embodiment of the illumination, the system includes an illumination means and a second assembly of metal channels arranged in a single plane, one end of which is significantly closer to the viewing area, and arranged so that this second assembly forms a second array for optical transfer of information around the viewing area, generally symmetrically relative to the first transfer array, with respect to the viewing area. It could also be possible that the second assembly be staggered vis-à-vis the first.

In this alternative, the system preferably comprises means for optical coupling between the ends far away from the viewing area and the illumination means, which makes it possible to couple inside the channels the light from an external beam and to focus it on the viewing area, and thus to obtain a particularly effective illumination.

The invention also relates to a system for optical detection as described above comprising an illumination means and a second assembly of metal channels arranged so that said second assembly forms a second array for transfer of optical information symmetrically to the first transfer array, with respect to the viewing area, the first and the second assemblies being buried under the viewing area at a depth lower than the wavelength, the first and the second assemblies being connected to each other by a network of parallel channels separated from each other by a distance lower than the radiation wavelength.

According to various embodiments, the parallel channels may be of constant section or they may be modulated by a short-length modified section, that is to say, shorter than the wavelength, and having a width lower than, equal to or greater than the rest of the channel to inhibit the greatest part of the transmission of the direct plasmon by impedance change and by forcing transmission to be made by the evanescent fields around the modified section, this configuration making the system more sensitive to the presence of the particle in the groove above said connection between the arrays.

In case the array wires are buried and extend under the viewing area, the illumination coupling means can be a buried array too, in which the ends at the side of the viewing area are connected by a metal and a plasmonic contact to the decoupling channels. In this case, the particles of the viewing area above the buried plasmonic channels act to modulate or change the transmission of the illumination along these wires. The connection between plasmonic channels under the viewing area can then be defined so as to limit the direct flow of plasmonic channel of illumination and optimize the modification made by the particle located above, particularly if it has the shape of a constriction of a subwavelength size which reduces the plasmonic coupling to a tunnel effect between the illumination array side and that of the decoupling array.

The illumination means can operate in integrated optics and be located in the plane of the second transfer array.

Preferably, the optical coupling means include network extractors/couplers located at the ends far away from the viewing area, thus providing an efficient transfer of light to plasmonic channels.

Preferably, the network extractors consist of a modulation of the width of the ends of the transfer arrays at the scale of the wavelength, therefore ensuring a good propagation of the incident light through the plasmonic channels, especially if the light comes from the axis vertical to the channels.

In another alternative, the optical coupling means include network couplers located at high index dielectric wires which are arranged at the end of the channels far away from the viewing area and in the extension of these channels.

In a particular embodiment of these network couplers, these couplers consist of a modulation of the width or of the section of the dielectric wires.

In another particular embodiment of these network couplers, these consist of perforating holes in all or part of the central dielectric wires.

According to a second alternative embodiment of the illumination, the system includes an illumination means directly illuminating the viewing area and a second assembly of metal channels arranged to form a second array of optical information transfer around the viewing area.

In this alternative, it can be projected that the system comprises a plurality of arrays parallel to the same plane and located at different heights with respect to the viewing area. These arrays, stacked on each other at different heights, have the advantage of being formed so as to facilitate the removal of aberrations by an adequate arrangement.

Thus, preferably, the heights and the geometric characteristics of the arrays are determined in a way such as to introduce a chromatism depending on that of the optical detection means, thereby compensating for the chromatism of the optical detection means—preferably including a microscope objective—to obtain an image devoid of chromatic aberrations.

Also preferably, the system includes means for compensating the transverse geometric and chromatic aberrations of the image reconstructed by the optical detection, which improves the quality of the image.

In a particular embodiment, at least one plasmonic channel has a modified section at its end closest to the viewing area, for the impedance matching of the optical information from this viewing area.

In another particular embodiment, at least one array of optical information transfer is provided with electrical contacts for the control of the electrostatic potential and the attraction or the repulsion of particles in the viewing area.

In another particular embodiment, at least one array for optical information transfer is provided with electrical contacts for the control of electrochemical reactions in the viewing area.

The invention also relates to an equipment for detecting optical particles, comprising a plurality of basic systems for optical detection of particles according to one of the above embodiments and arranged on a single substrate. This equipment makes it possible to benefit from the advantages of the aforementioned basic system as well as collective manufacturing techniques of such basic systems. The superstrate acting as a lid can also take advantage of these techniques, and may, generally, complete the functionalities which will be provided to the substrate by the spread of these teachings.

In a particular embodiment of this equipment, basic systems form a network in the plane of the substrate.

Preferably, at least one fluid circuit attaches at least two optical detection basic systems to each other.

In a particular alternative, at least two basic systems form the arms of an interferometric device, the viewing areas associated with each of these basic systems being substantially close to each other. The interference signal between the two arms thus, makes it possible to reveal the presence of a nanoparticle in a particularly sensitive way.

For the analysis of particles motion, it can be projected that the equipment includes means for analyzing real-time optical signals collected by the optical detection means in the far field and by the deduction of the detected movements in the viewing area.

The invention also relates to a method for manufacturing a system for optical detection of particles. This method includes a step of performing a lithography on a metal layer deposited on a substrate for the constitution of metal plasmonic channels on a single plane of the substrate so that one end is close to a viewing area that can be illuminated by a radiation with a determined wavelength. In this method, during the lithography step, the channels are arranged so that this assembly forms around the viewing area an array for optical information transfer, the value of at least one spatial characteristic of the array being lower than the wavelength at the ends of the channels near the viewing area, the value of at least one spatial characteristic of the array being higher than the wavelength at the ends of the channels far away from the viewing area. In addition, this method also includes a step for arranging means for optical decoupling between these ends far away from the viewing area and an optical detection means for.

Finally, the invention relates to a method for manufacturing an equipment for optical detection of particles. This method consists of placing, on a single substrate, a plurality of basic systems for optical detection of particles obtained by the manufacturing method described above.

According to an alternative of this method, it comprises an additional step of performing a lithography on a substrate for providing at least one groove so as to form at least one fluidic channel connecting to each other at least two optical detection basic systems.

BRIEF DESCRIPTION OF THE FIGURES

Other characteristics and advantages of the invention will appear upon reading the description that follows, with reference to the accompanying drawings, which illustrate:

FIG. 3, a schematic top-view of an optical detection system according to a second embodiment of the invention;

FIG. 4, a schematic cross-sectional view of the optical detection system according to this second embodiment of the invention;

For the sake of clarity, same or similar elements are identified by identical reference numerals throughout the figures.

DETAILED DESCRIPTION OF AN EMBODIMENT

Figure 1:
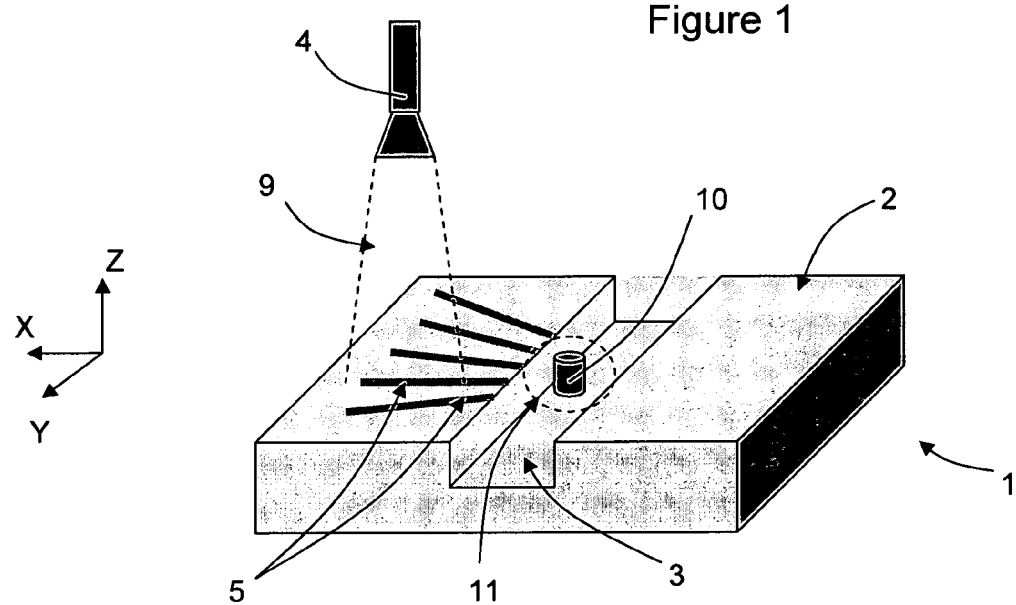
FIG. 1, a three-dimensional view diagram of a system for optical detection according to a first embodiment of the invention.
Figure 2:
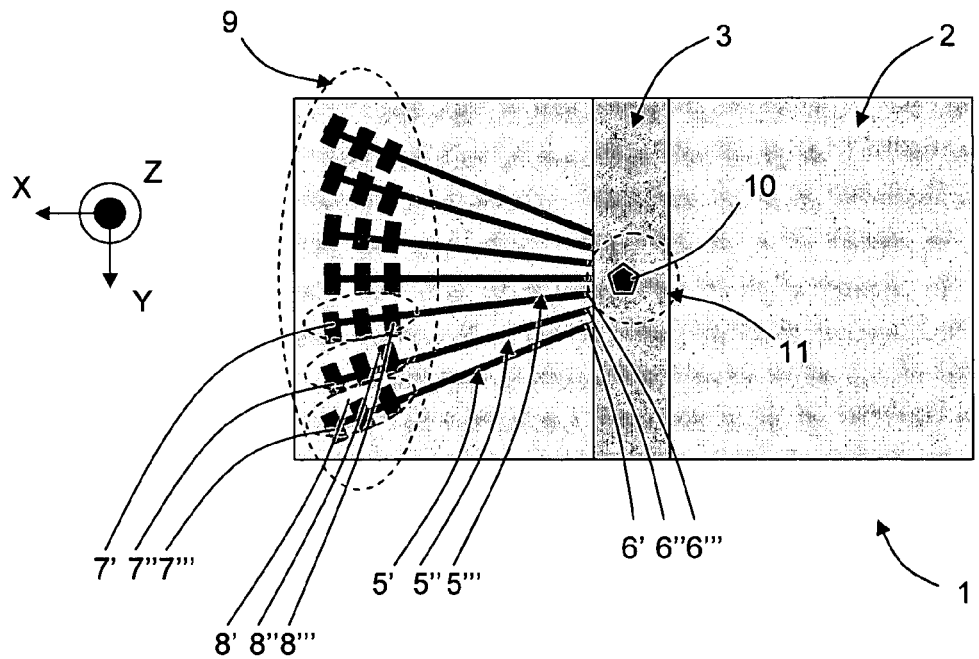
FIG. 2, a schematic top-view diagram of the system for optical detection according to this first embodiment of the invention.

With reference to FIGS. 1 and 2, a system for particles detection according to a first embodiment of the invention comprises:
- an illumination means (not illustrated),
- a optical detection means 4,
- a substrate 2 in which a groove 3 is dug,
- a viewing area 11 within the groove 3, comprising particles 10, and
- an assembly 5 of metal plasmonic channels 5', 5" and 5''' forming an array.

The metal plasmonic channels 5', 5" and 5''' are made up of wires arranged in an array, so that their whole constitutes multi-mode means making it possible to capture without scanning an information in a field and transcribing it magnified. This array couples a subwavelength near-field zone 6 (the viewing area 11) to a recessed area 7 where the metal wires are wider apart and allow the radiation of the information gathered locally and enlarged at the passage of the array 5 towards detection means 4.

To allow a transfer of the optical information from the subwavelength near field to the far field, the distance between two adjacent wires 5', 5" and 5''' is lower than the wavelength at the ends 6', 6" and 6''' near the viewing area 11, and the distance between two adjacent wires 5', 5" and 5''' is higher than the wavelength at the ends 7', 7" and 7''' far away from the viewing area 11.

The substrate 2 enables the array to be held when placed on it. Said substrate may be made of glass or silicon coated with a layer of amorphous silicon of 100 nm to 30000 nm typically. Polymeric supports may also be considered, among the transparent plastics (poly-methyl-methacrylate, cyclo-butyl-benzene, ABS, PVC, polypropylene, or from elastomers or silicone (polydimethylsiloxane (PDMS) and its derivatives), or even from polymers such as polyimide and Kapton. A support of a higher index oxide may also have some interest for plasmons. Oxides such as lithium niobate, sapphire (Al2O3) or quartz are also possible options.

These metal wires can be obtained using techniques of cutting a thin uniform metal layer by lithography, such as a resin and an electron beam exposure, taking into account the scales to be reached.

The expansion degree, width and height of the enlarged sections are optimized so as the near-field information is best conveyed in the enlarged part 7 of the array. The skilled person will be capable of producing such optimizations. For example, the thickness can be optimized first, either at the value having the best compromises for losses, or at a slightly higher or lower value, given the delicate aspects of the system's overall optimization. Then, the angular difference can in turn be optimized between two wires of the array—and if possible its regularity—and the fraction of the remaining metal, especially in the viewing area and the enlargement area of the mode.

A skilled person will notice here that the wavelength of the light that can be transmitted through these metal wires is largely predetermined by the metal of the wires, for example silver, due to plasmonic resonances which do not guarantee a higher resolution than in a wavelength low field. However, in this latter case, if the resolution is not increased, it can remain of the same order of magnitude as a good microscope objective in the far field. In addition, a length between 3 and 300 micrometers would be suitable for these wires, determining the exact length to be chosen depending on the attenuation of the plasmon used along the variable path, because of plasmonic losses, and therefore, in particular, on the light frequency used.

The angle between the metal wires of the array depends on their number. For about twenty wires, there should be an angle of about 0.10 radians. The wires thus, reach a separation of one micron to about ten microns. To decouple the contained information toward the free space, the period of corrugation is substantially equal to the wavelength in the vacuum divided by the effective index of the plasmon mode in the wire at the extractor. Indices of 1.5 and a wavelength of 600 nanometers lead to a modulation period with a width of 400 nanometers in the decoupling. Higher effective indices, specific to the superresolution, lead, in principal, to even weaker periods, but if one wants the wires to work in this regime at the extractor, then one can work at a higher order to couple, thereby approaching a period between one half and one wavelength, according to the emerging environment.

According to the preferred embodiment, a hole 3—or even arrangement or groove—is arranged in the substrate at the viewing area 11, for example to pass a nanofluidic channel in which particles of interest 10 are to be detected.

The viewing area 11 may for example be a cylinder of vertical axis Z, around which are arranged the metal wires 5', 5" and 5'". Such a cylinder may have a diameter of about 400 to 1000 nanometers.

In a particular embodiment, this hole 3 comprises localized chemical fictionalizations of the surfaces of the viewing area 11 making it possible for example to selectively anchor additional reactive species as surface chemical "keys" of the nanoparticles to be analyze.

The decoupling means 8 allows to decouple the light in the wires 5', 5" and 5'" towards usable light for imaging. For this purpose, this means is constituted, for each wire 5', 5" or 5'", of a network extractor 8', 8" or 8'" located in the enlarged part 7 of the array, of adjusting the width of the tips of the array at the scale of the concerned wavelength. This width modulation is a modulation of the effective index. If the diffraction condition is adequately met, the plasmonic modes transmitted by the periodicity spread significantly along the vertical axis Z.

The periodic pattern of the networks 8', 8" and 8'" at the end of the wire is designed to maintain the integrity of the wire. If the wire is 30 nanometers wide at first, it must be about 100 to 250 nanometers wide at the end, that is to say less than a wavelength. With an angle of 0.010 to 0.015 radians between the sides, the wire reaches at the top of the range and after about 10 microns a 180 microns width, which corresponds to the desired order of magnitude.

The modulation is progressively graduated along the wire to better radiate the energy and the information it carries. A maximum modulation at the aforementioned scales consist in reducing locally the width of the wire to half—120 nanometers—with a ratio of 1:2 between the large and small parts.

The periodic pattern may also be focusing on the entire array. For equal excitations of wires at the narrow input of the array and for a light focalization at 250 microns above the array, the angles associated with this part of the path in the superstrate (air, or liquid, or polymer) would be in the range of a vertical tilt of 15/250, therefore less than 0.1 radians. However, this is about rays that reach the optical axis, and which are not representative of the whole image, which may include more tilted rays.

The detection means 4 is a classic far field detection means, for example a microscope objective. It is arranged along the vertical axis Z so as to collect the light diffracted by the decoupling means 8. A large aperture collect objective is preferred, in order to collect the information at the highest spatial frequency, a frequency which corresponds, in the decoupling zone, to the alternation of the electric field signs—seen as a scalar field—between two adjacent wires. In the aforementioned example, a minimal numerical aperture of 0.7 is required, since the typical difference between two decoupling elements is about 1.5 microns.

A fundamental aspect of this system 1 is that the local optical information of the viewing area 10 is still available in the form of distribution of the phase of each radiating wire. A disruptive object 10 to be detected in the viewing area 11 generally influences more than one metal wire of the array, and thus it is the collective radiation of the rear parts of the array that is captured, the direction of this radiation revealing the phase relationship between the various components. Thus, for a convenient choice of periodicities, the system according to the invention may have an arbitrary enlargement. Thereby, the apparent position in the plane object of the microscope 4 objective placed on the array makes it possible to view the object in the viewing area 11, near the narrow side of the array 5.

Figure 16:
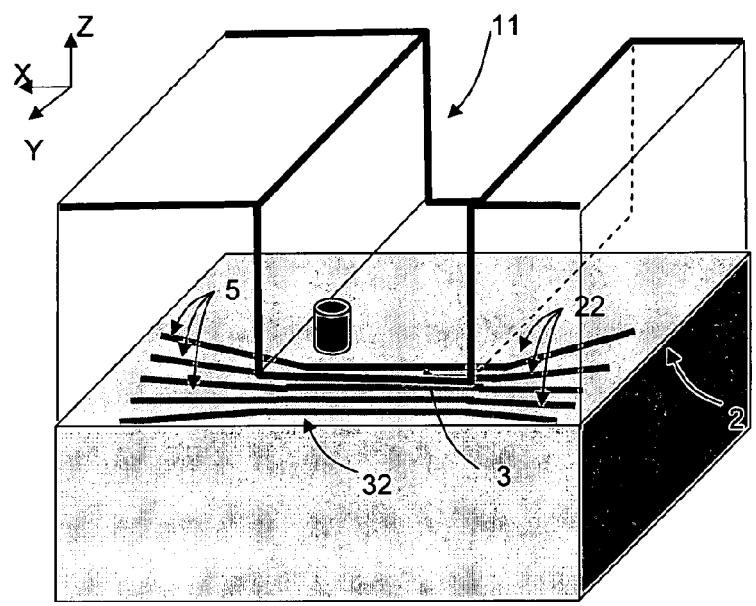
FIG. 16, a three-dimensional schematic view of an optical detection system according to an eighth embodiment of the invention.
Figure 17:
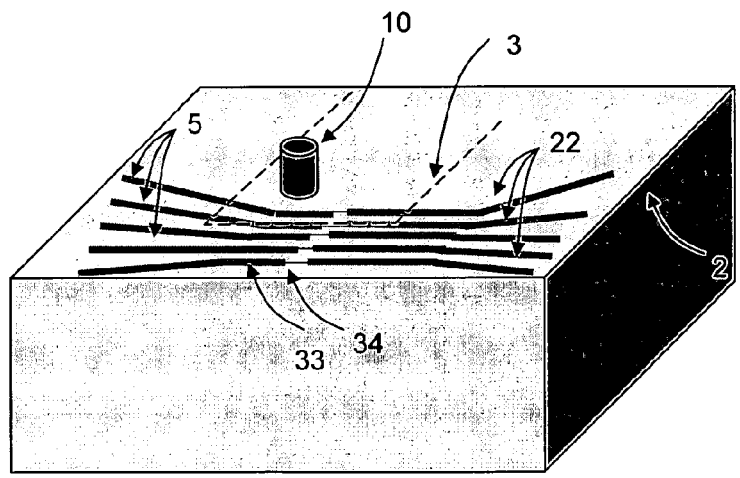
FIG. 17, a three-dimensional schematic view of an optical detection system according to a ninth embodiment of the invention.

FIGS. 16 and 17 illustrate an embodiment in which the wires 5', 5" and 5'" are buried in the substrate, i.e. located in holes dug in the substrate.

In case the wires of the array are buried, as shown in FIGS. 16 and 17, the wires 5', 5" and 5'" can extend under the groove 3 at a subwavelength depth under this groove and are capable of providing information in the viewing area 11 on the presence of a particle 10 near the bottom of said groove 3. A particle 10 that is too high above the bottom cannot, however, be seen with such a resolution as a particle near the bottom.

A second embodiment of the invention is now described, comprising a means of illumination, with reference to FIGS. 3 and 4.

The illumination means of the object 10 includes a powerful source located in the vicinity of the viewing area 11. This source is coupled to the viewing area 11 by a coupling array 22 arranged symmetrically with respect to the decoupling array 5. Regarding the plasmon supported by silver Ag, the photons energy is typically between 3 and 3.5 eV, that is between 380 and 320 nm in the near UV. One can use either Xenon lamps or GaN laser diodes or helium-cadmium lasers about 325 nm or electroluminescent diodes (LEDs) or AlGaN laser diodes. LEDs in this range are routinely commercialized with unitary powers of about a few mill watts, and whose "brilliance" (Watt per square centimeter per steradian) is quite important. For the plasmon supported by Gold, the photons energy is typically between 2.2 and 2.5 eV, that is in the yellow-green spectrum part. LEDs cover these wavelengths, but often with modest brightness. Here, the double gas or solid lasers are good candidates (532 nm, 514 nm).

To emit light towards the viewing area 11, the source 4 emits first in the Z direction and on the zone 24 light in the direction of the coupling networks 23', 23" and 23'" at the ends of the coupling array. The light then couples in the XY plane by the metal wires and draws together in the viewing area 11 (arrow 25'). Therefore, light allows to illuminate the nanoparticles 10, then part of it crosses the metal wires 5', 5" and 5'" (arrow 25") before being decoupled by the networks 8', 8" and 8'" until the detection means 4.

In case the array wires are buried, as shown in FIGS. 16 and 17, the wires 5', 5" and 5'" can extend under the groove 3 at a depth below the groove which is lower than the wavelength, and connect by close channels almost parallel 32 to channels 22', 22", 22"' of the illumination system, which will also be buried in this case. It is the modification in the transmission along the thin plasmonic channels 32 joining the arrays under the viewing area 11 which provides then the sought information, an information that will be all the more stronger when the particle 10 will be near the bottom of said groove 3.

As shown in FIG. 16, the connector 32 which joins the arrays under the viewing area may be direct.

In another embodiment, shown in FIG. 17, the connector 33 joining the arrays under the viewing area can be modulated by a short-length modified section 34, that is to say, of lower length than the wavelength, and of smaller, equal to or greater width than the rest of the channel 32 to inhibit most of the direct plasmonic transmission by impedance change and by forcing the transmission to be made by the evanescent fields around the modified section, this configuration making the system more sensitive to the presence of the particle 10 in the groove 11 over said connection between the arrays.

Here, the skilled person will notice that attention should be paid to the chromatism of the system. This system tends indeed to function about a single wavelength, but short networks, as well as other network shape modulation alternatives—for example simultaneous registration of multiple networks in the metal structure—can make it particularly possible to have several wavelengths or a very large window to properly benefit from the advantages of the used plasmon. Yet, a fine adjustment of the extractor network pitch and its amplitude makes it possible to form in the superstrate (or substrate) a beam the wave front of which carries well-defined aberrations, these aberrations can therefore be compensated with those native of the far field 4 optical system, the whole resulting in an apparent absence of aberration. The apparent focal point of waves from a network in one of the array wires may thus be located above or below the substrate 2.

Figure 5:
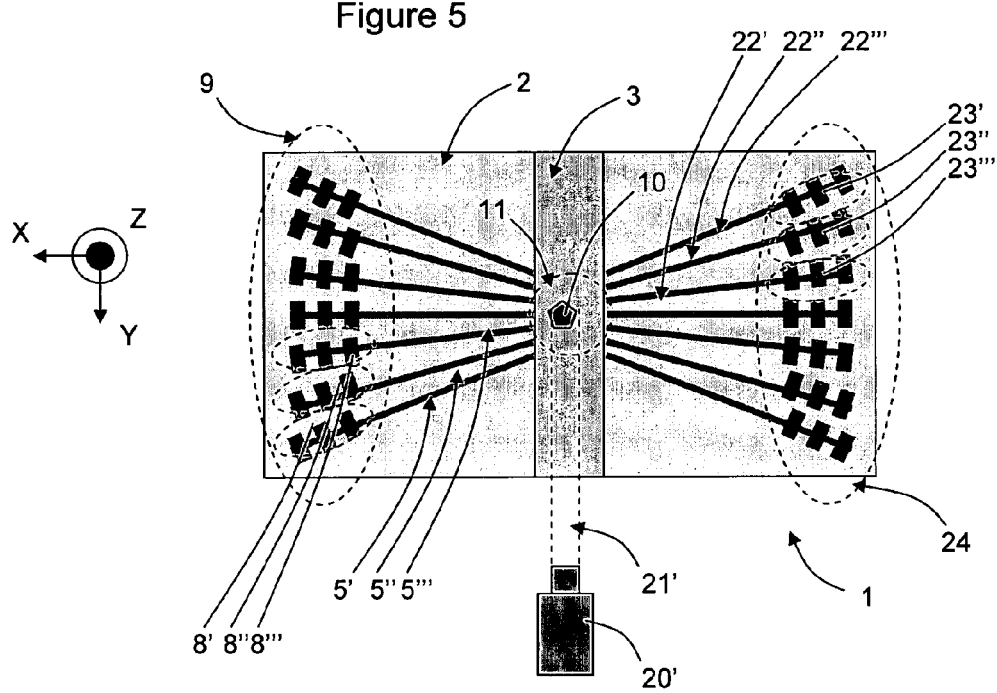
FIG. 5, a schematic top view of an optical detection system according to a third embodiment of the invention.

According to a third embodiment of the invention illustrated in FIG. 5, the two arrays are used for the decoupling of the optical information. Thus, the illumination means is a source in the third space Z dimension, straight out to the nanoparticles 10, for example an electroluminescent diode, a laser or any other directed light source.

Figure 6:
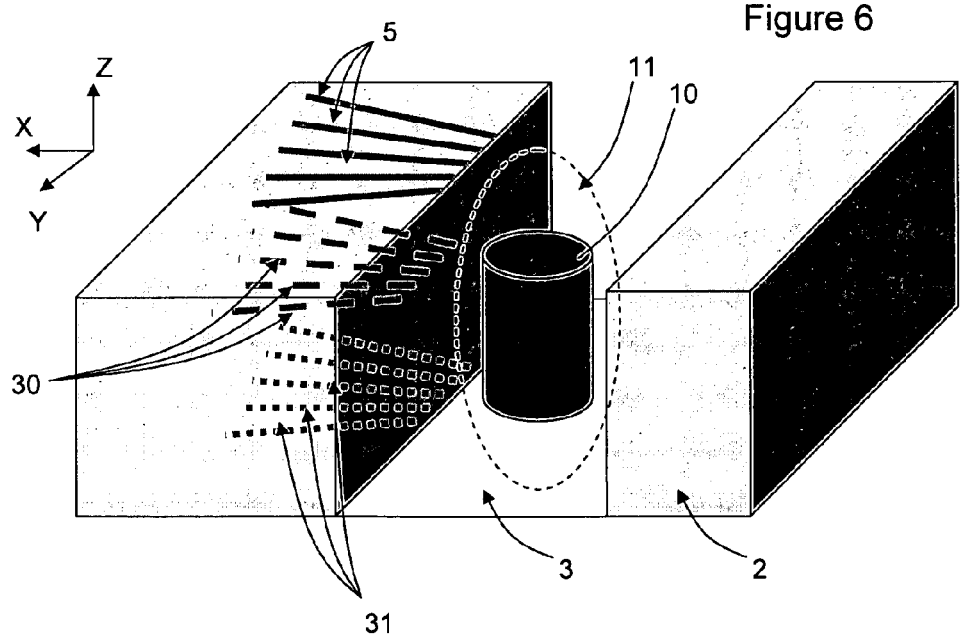
FIG. 6, a three-dimensional close-up view of an optical detection system according to a fourth embodiment of the invention.

Now, a fourth embodiment of the invention with a plurality of superposed arrays, with reference to FIG. 6 is described.

In this example, the system includes a plurality of arrays 5, 30 and 31 with metal wires arranged on the same side of the groove 3, in parallel and along the same XY plane, but at different heights along the axis Z. Each array 5, 30 or 31 is similar to that described in the first embodiment of the invention. This system is achieved by successive depositing and structuring of arrays, from the first—the deepest—up to the last—the most superficial.

Adjacent arrays are separated by a spacer layer (not illustrated) of dielectric nature. These layers may be made of oxides, nitrides or organic materials commonly used in nanotechnology, such as the butylcyclobenzene.

At the viewing area 11, the starting points of the metal wires are defined as a group of points around a parallelepiped corresponding for example to the microfluidic channel. According to other embodiments, other forms of these starting points may be considered, namely a spherical or ellipsoidal shape. These shapes may be adapted to the intended fluidic channels. Thus, some of the fluid constraints (establishment of a laminar or turbulent flow, for example) and of the physic-chemistry can be taken into account by choosing an appropriate shape.

At the decoupling networks (not illustrated, but identical to those of the first aforementioned embodiment), it is necessary to take certain precautions to avoid shading effects between the diffraction means from the various arrays which are stacked on top of each other. For this purpose, the metal wires of the deep arrays may be provided such that they are extended beyond those which are less deep.

In a non illustrated particular alternative of this fourth embodiment, at the opposite side with respect to the groove 3 of the decoupling arrays 5, 30 and 31, the illumination means is coupled to a plurality of optical information coupling arrays. These coupling arrays are similar to those described in the second embodiment above. The illumination means may be a source of direct light. Thus, this provides a stronger coupling of the arrays with the illumination means and a more evenly distributed illumination over the entire viewing area 11.

According to alternatives using a plurality of superposed arrays, said arrays are arranged and have characteristics enabling them to introduce a predetermined chromatism. The arrays located at different heights and which have decoupling networks more or less distant from the center may have network characteristics (modulation period and amplitude) such that they direct the beams around a real or virtual convergence point. Therefore, the area around this point of convergence becomes conjugated to the region imaged in the center and gives a magnified report. Chromatic effects may thus be deliberately introduced into the system, similarly to a diffractive optical lens. The average angles of the emergence of beams having different wavelengths move along a network law with an incident beam on the network having an effective index of the array wire considered.

According to other alternatives of the invention, the system also includes aberration correction means. These means may consist of a purely optical compensation, or of a further processing of a large amount of information, for example by capturing images at several focalization depths of the recovery external optics.

Figure 7:
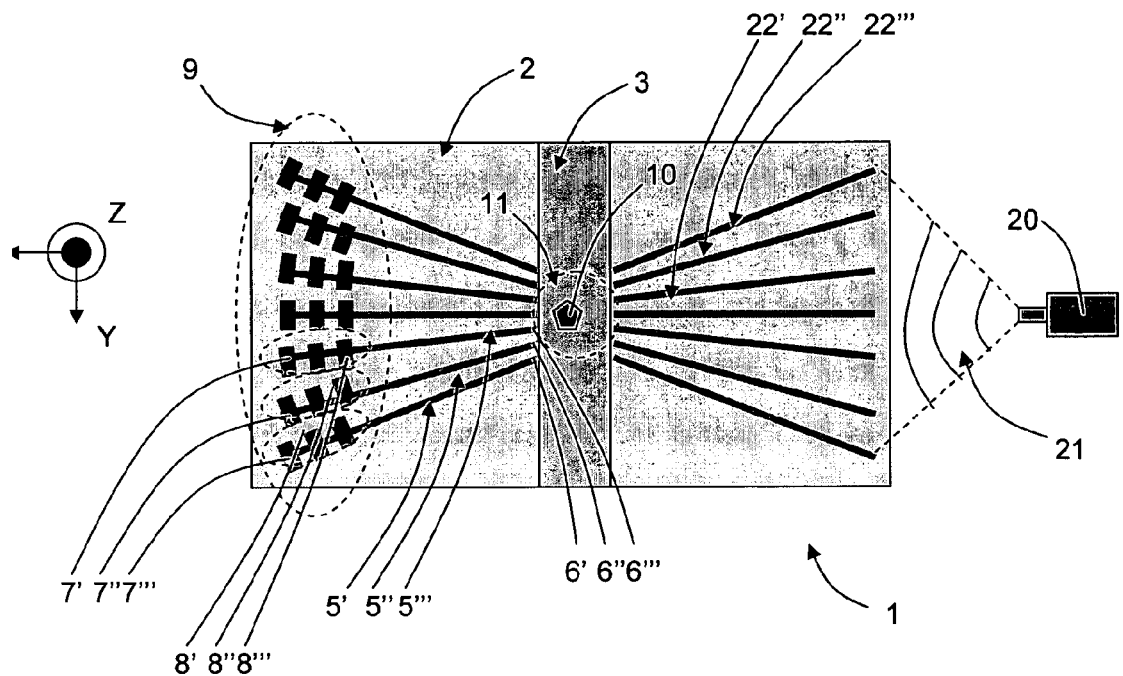
FIG. 7, a schematic top-view of an optical detection system according to a fifth embodiment of the invention.
Figure 8:
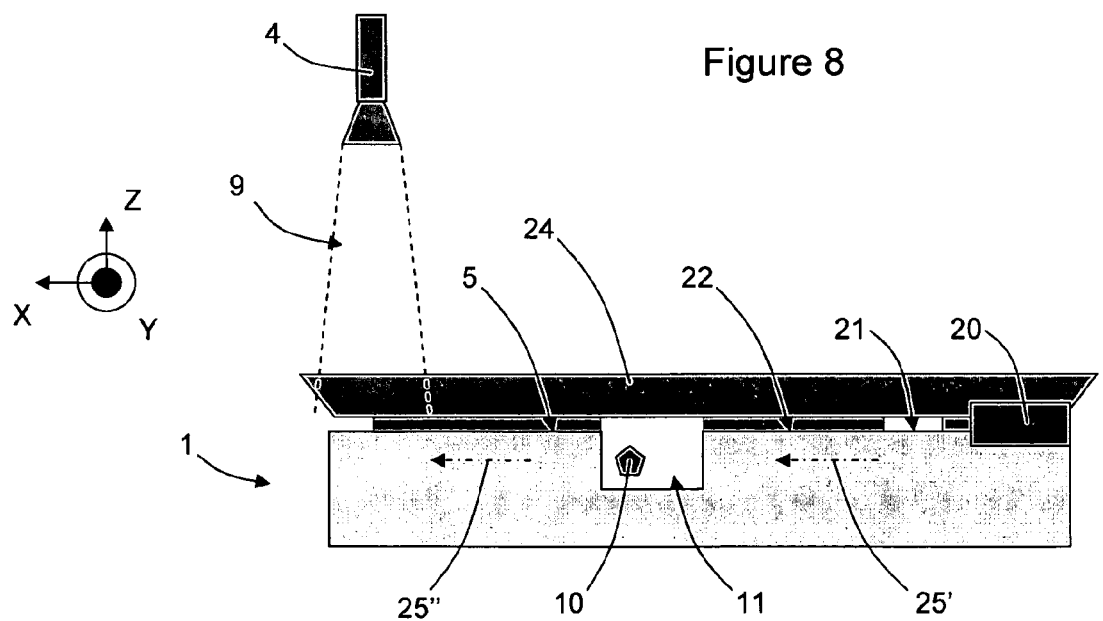
FIG. 8, a cross-sectional view of the optical detection system according to the fifth embodiment of the invention.

In a fifth embodiment of the invention illustrated in FIGS. 7 and 8, the illumination means 21 comprises an integrated optics lighting element, the axis of which is located in the substrate 2 plane, for example using reported sources, pumped photos or electrically pumped photos. This illumination means is coupled to the array 22 so as to direct the electromagnetic excitation to the frequencies of light up to the viewing area 11.

According to another alternative of this fifth embodiment, the illumination can be directed directly to the viewing area 11 by a beam from a source integrated on the substrate 2.

Figure 9:
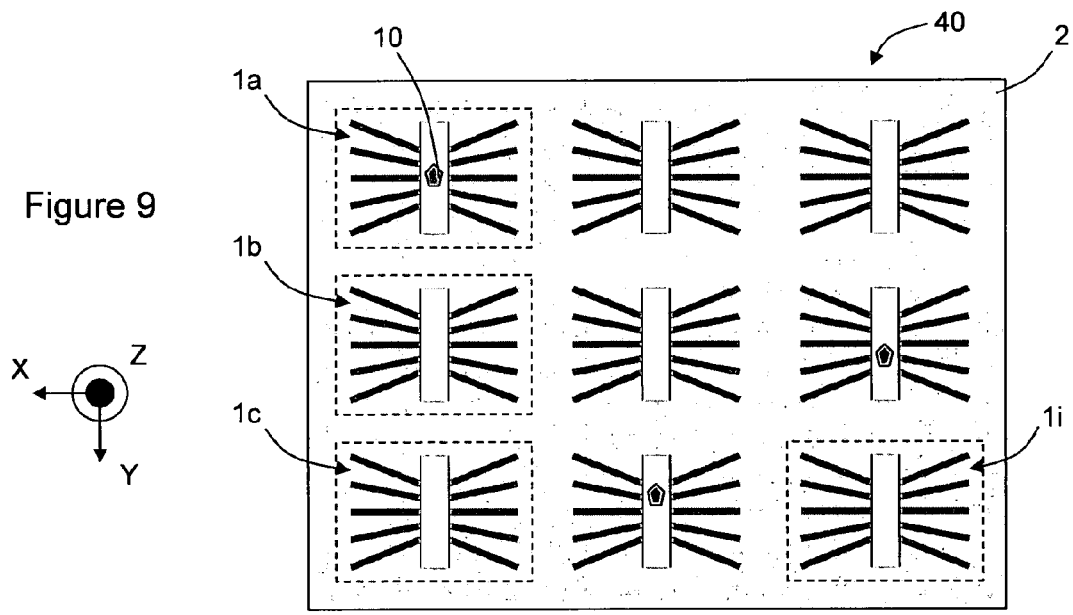
FIG. 9, a top-view of a first alternative of an optical detection equipment according to a sixth embodiment.
Figure 10:
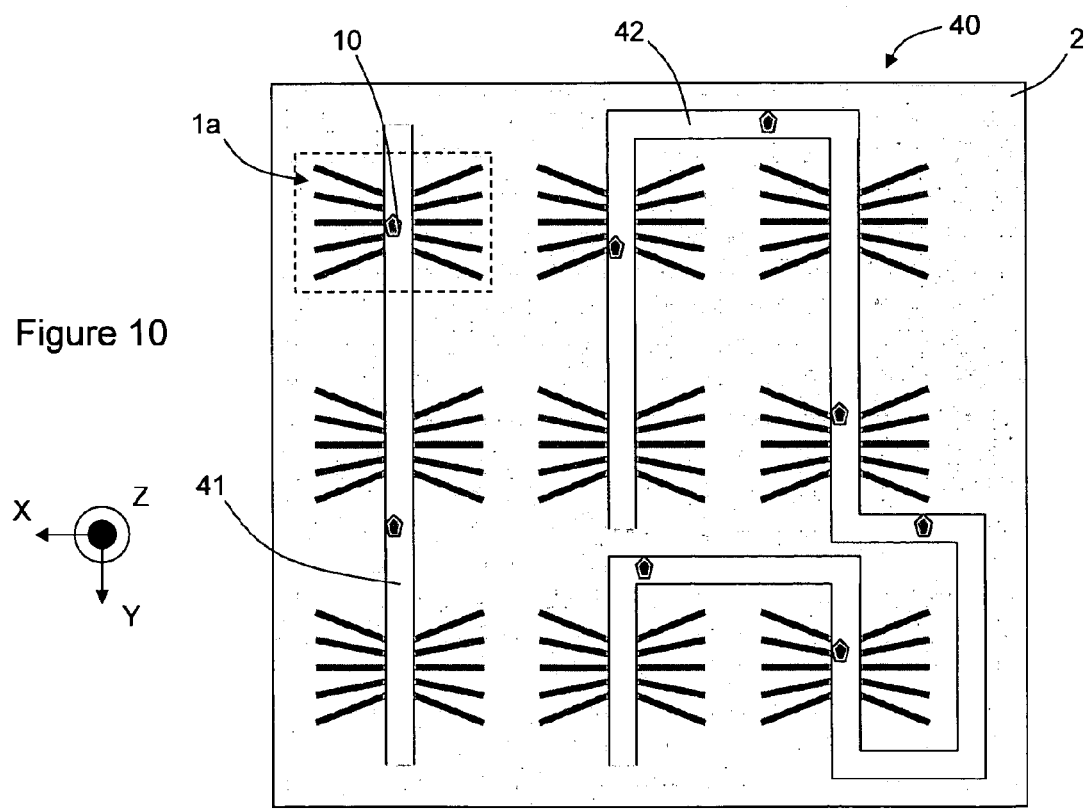
FIG. 10, a top-view of a second alternative of this optical detection equipment according to this sixth embodiment.

Now, a sixth embodiment of the invention comprising a plurality of basic detection systems, with reference to FIGS. 9 and 10 is now described.

The embodiment of FIG. 9 corresponds to an equipment 40 for optical detection of particles 10, said equipment comprising a plurality of basic systems 1a to 1i for optical detection of particles. These systems 1a to 1i are arranged on the same substrate 2. Thus, it is possible to take advantage of collective manufacturing techniques. It should be noted here that the distribution of basic systems may be one-dimensional or two-dimensional.

According to the alternative suggested in reference to FIG. 10, nanofluidic circuits may be included in relation to the basic network systems. Viewing areas are regularly distributed around a right channel 41 or a more complex topology channel 42. Based on the systems to be joined, the channel may be curved, spiral, with meanders, etc.

These microfluidic channels are defined in the equipment by use of pre-defined marks, allowing the alignment of the land marking of the etching masks of the channels with respect to arrays (or vice versa). Then the equipment is provided with lids and openings, allowing the control of the flow of fluids in the viewing areas.

According to an alternative of FIG. 10, the viewing areas are arranged around vertical and oblique channels of a "microfluidic chip," in channels of access to the main circuit located, for its part, in the plane of the chip, and consisting in one or more planes of stacked micro-pipes.

For elastomeric flexible material chips, such as polydimethylsiloxane (PDMS) and its derivatives, it is possible to maintain a compatibility with the flexibility of the chip by changing the plasmonic circuits so that they consist of a succession of micronic metal islands very close to each other. Thus, the optical information communication means—the arrays—accommodate the deformations of PDMS chips. This differs from a continuous metal wires structure, which would unexpectedly break and exhibit deteriorated optical characteristics. Nano-breaks performed a priori make it possible to avoid this type of problem and make the equipment more tolerant.

In a particular embodiment of the invention, a wire exhibits at its end closest to the viewing area 11 a section—or "gap". This end can then satisfy the conditions of impedance matching of information from the viewing area to the corresponding wire, similarly to the practice of microwave guiding by means of intermediary information, typically having one quarter of the wavelength of the local information to be communicated.

To recover the fluidic channels of the equipment, this latter is covered with a thin lid, which may be particularly thinned in the areas of optical recovery, for example thinned to less than 250 microns in the part where the collection of light is achieved.

Figure 11:
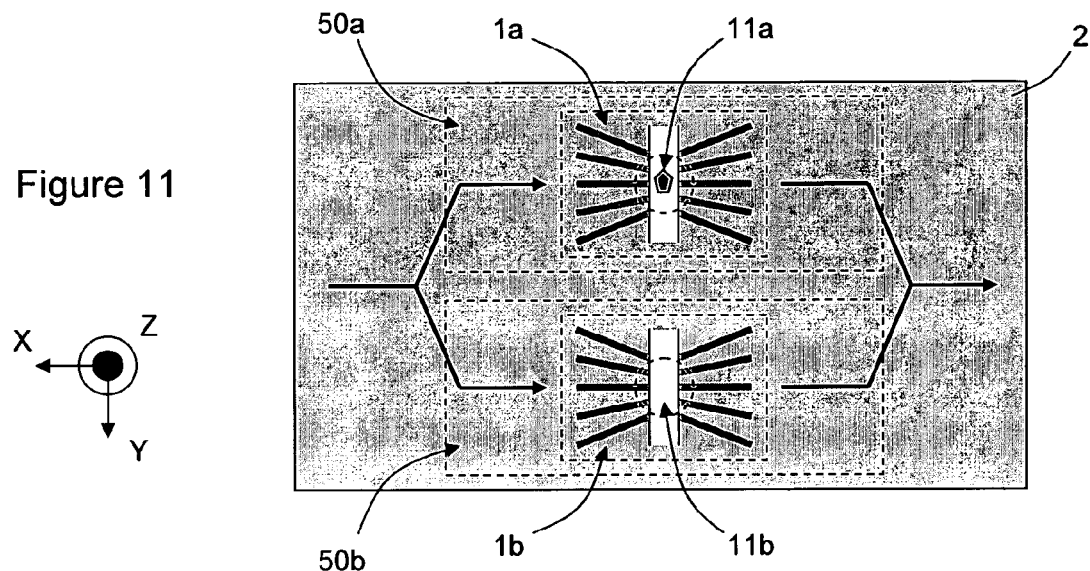
FIG. 11, a top-view of an optical detection equipment according to a seventh embodiment.
Figure 12:
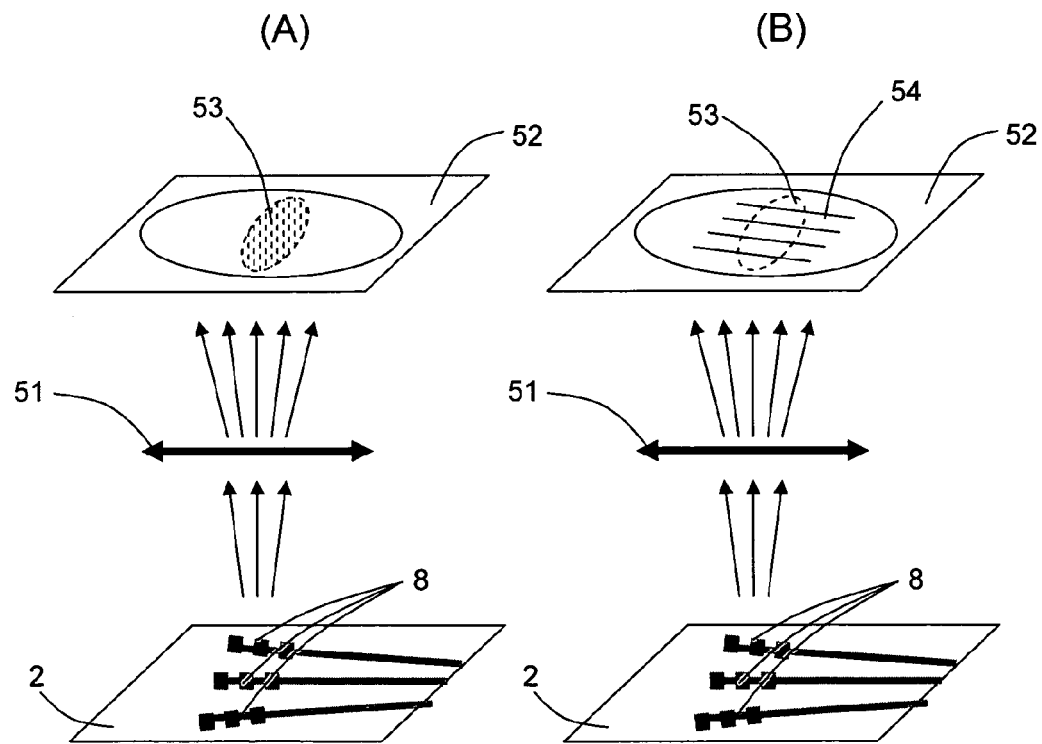
FIG. 12, a three-dimensional close-up view of this optical detection equipment according to this seventh embodiment.

A seventh embodiment is now described, of the interferometric type, with reference to FIGS. 11 and 12.

This equipment uses the sensitivity of interference systems for the weak signals. For this reason it is necessary to consider the assembly of two arrays converging from both sides of a viewing area 11a like an optical system located in one arm 50a of an interferometer. Said interferometer may be of Michelson, Mach-Zehnder, Twyman-Green type or the like. The separator is preferably arranged upstream from the illumination coupling areas, then another separator (or the same in a Michelson) is used downstream in the direction of the collection. Thus, the passage of light in two arms can be used and the phase information is compared. A reference arm 50b is added to the first arm 50a, this second arm 50b being based on a viewing area 11b adjacent and substantially identical to the first viewing area 11a. Under these conditions, the interference signal 53 between the two arms 50a and 50b, obtained in the plane 52 of the detection means via the objective 51 of the latter, can reveal the presence of a nanoparticle. The transverse dimensions of the viewing area which are used here so as to see a signal having phase shifts depending on the position.

It should be noted here that it is possible to introduce a phase shift at the output of the system, outside the arrays, to get into a situation where the viewing field is striated with straight line fringe to the balance between the two paths. Therefore, a deviation from the perfect balance appears as a local modification of the fringes 54, corresponding to changes in position and contrast revealing the phase and amplitude of the disturbance.

In terms of the sharing of a microfluidic channel and of the viewing area, several advantages in the electrically conductive array are observed, in addition to that of being a conveyor of optical information. When there is no electrical connection between the wires of the array, these can serve as electrical conductors. They can then impose predefined potentials in the viewing area. These potentials may have attractive or repulsive roles for charged particles. They may on the contrary screen space charges to allow non-neutral particles to reach target interaction sites. They may also allow the development of nano-actuators of the type MEMS or NEMS in the viewing area, for example of the moving parts that affect the channel's hydraulic conductance, or on the local thermal. Another possibility is to conduct in situ the functionalisation by suitable electrochemical reactions, as particularly performed on gold layers supporting usual surface plasmons. To practice such a functionalisation of measurement, a lithography defining small openings may be used and through which the chemical treatments in vapor or liquid phase are applied and the functionalisation elements are brought chemically or physicochemically, for example by electrostatic bonding.

In a particular alternative of this seventh embodiment, it is expected to have an CMOS type electronic interface circuit to usefully contact the array wires. This type of sensor is commonly used as a readout circuit of GaAs gallium arsenite matrices or other. This circuit then interfaces the network of the arrays wires outwardly, more specifically towards a computer equipped with adequate steering interfaces.

Lastly, a system for external reading can be designed, collecting in the outer parts the convenient features known on the conventional microscopes. It may be fitted with attachments for conventional microscopes, such as polarizers, diaphragms of field and aperture, color filters, notch filters. This helps promote the increase of signal to noise ratio relative to nanoparticles of interest.

Figure 13:
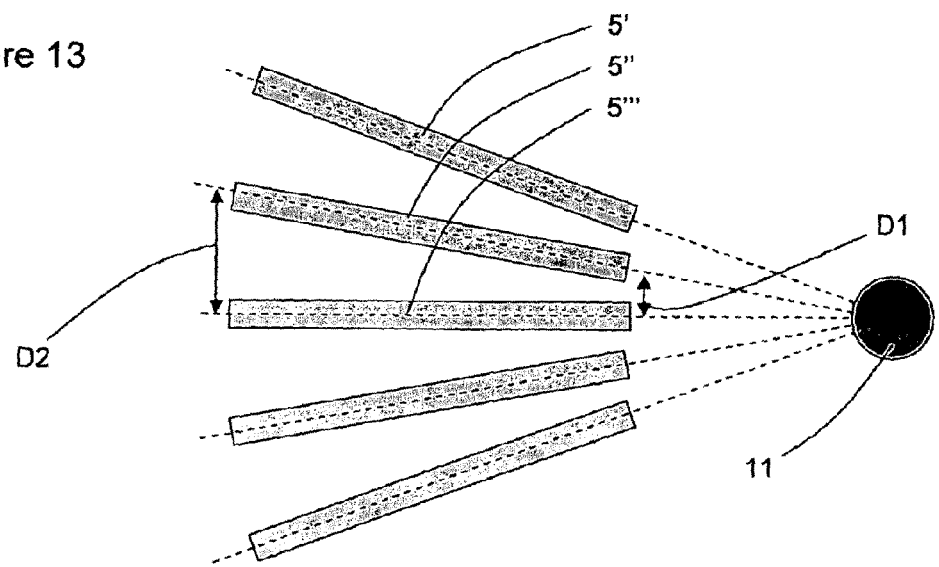
FIGS. 13 to 15, diagrams illustrating various alternatives of the array of metal plasmonic channels.
Figure 14:
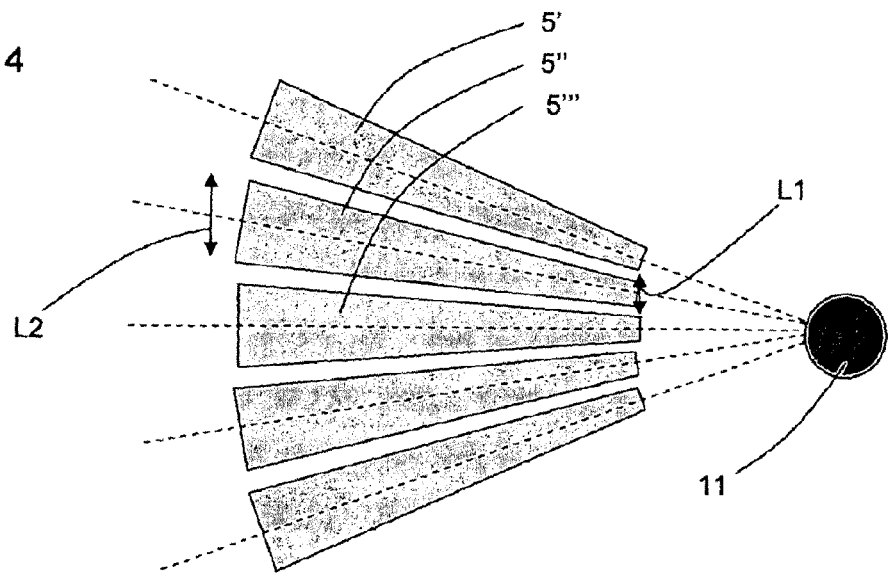
Figure 15:
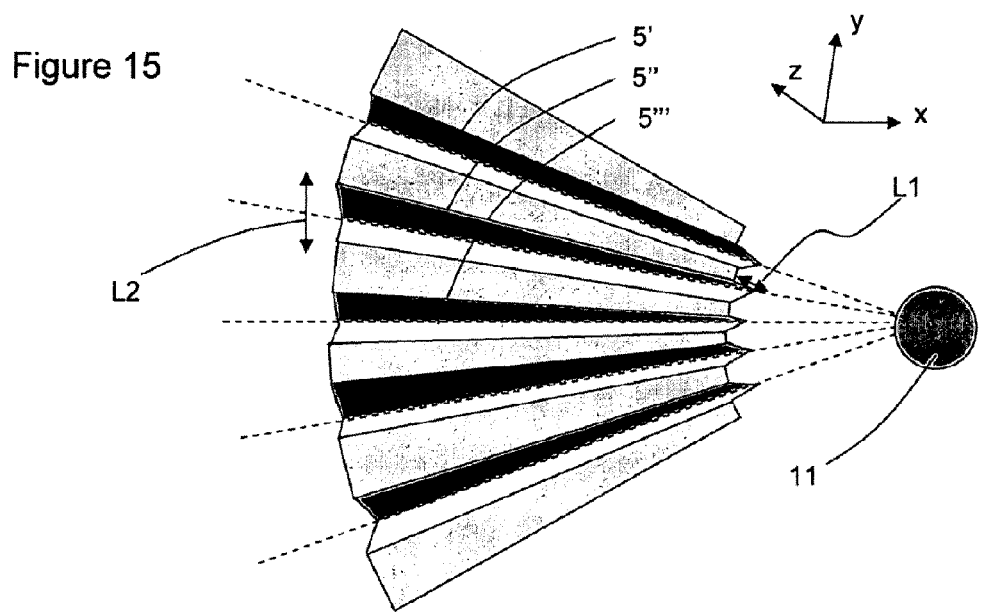

Finally, referring now to FIGS. 13-15, various alternative embodiments of the array of plasmonic metal channels are possible.

In a first alternative (FIG. 13), the plasmonic metal channels 5', 5" and 5'" are metal wires of constant width and the spacing between two adjacent wires increases between the near ends (D1 spacing smaller than half-wavelength) and the far ends (D2 spacing larger than half-wavelength) of the viewing area.

In a second alternative (FIG. 14), the plasmonic metal channels 5', 5" and 5'" are also metal wires and the spacing between the wires is identical at both ends, but the wires have a width which increases between the ends near and far from the viewing area.

In a third alternative (FIG. 15 showing a three-dimensional view), the function of the metal wires is provided by plasmonic channels supported by V-grooves in a thick metal film, and the tilt angle of this V is steeper at the ends near the viewing area 11 and less steep at the far ends. Moreover, these grooves 5', 5" and 5'" have a width which increases between the ends near and far away from the viewing area.

These different alternative embodiments of metal plasmonic channels may also be combined.

The aforementioned embodiments of the present invention are given only by way of non-limitative examples. It is obvious that the skilled person is able to carry out various embodiments of the invention without departing from the scope of the patent.

In particular, a skilled person will notice that the use of the fluidic channels or grooves is the preferred usage, but these channels are not essential to obtain nanoparticles optical signals. Indeed, the manufacture of the system by metal lithography may make it possible to leave small blocks at strategic positions in the viewing area, so as to collect signals of the presence of a nanoparticle in the absence of fluid or in the absence of a channel or groove. This can be a significantly calibrated case, advantageous in the implementation of the device for the detection of early signals or the calibration of the weak signals.

The invention claimed is:

1. A system for optical detection of particles arranged in a viewing area suitable for being illuminated by radiation with a predetermined wavelength, said system comprising optical detector, and an assembly of metal plasmonic channels arranged in a single plane of which one end is proximate to the viewing area to allow optical information resulting from the illumination of the particles arranged in the viewing area to be transferred from one end to the other of said channels, said channels being arranged so that said assembly forms around the viewing area an array for transferring said optical information, the value of at least one spatial characteristic of said array being lower than said wavelength at the ends of said channels proximate to said viewing area, the value of at least one spatial characteristic of said array space being higher than said wavelength at the ends of said channels distant from said viewing area, said system further comprising an optical decoupler between said ends distant from said viewing area and said optical detector, the optical decoupler configured to decouple the optical information being transferred to the ends of said channels distant from said viewing area to usable light for imaging, the usable light for imaging being collected by the optical detector in order to perform the optical detection of the particles being arranged in the viewing area.

2. The optical detection system according to claim 1, wherein the value of at least one spatial characteristic of the array of channels is lower than half the wavelength at the ends close the viewing area.

3. The optical detection system according to claim 1, wherein one spatial characteristic of the array of channels is the distance between two adjacent channels.

4. The optical detection system according to claim 1, wherein one spatial characteristic of the array of the channels is the channel width.

5. The optical detection system according to claim 1, wherein the plasmonic metal channels are made of metal wires.

6. The optical detection system according to claim 1, wherein the plasmonic metal channels are made of V-grooves dug into a metal layer.

7. The optical detection system according to claim 6, wherein a spatial characteristic of the array of the channels is the depth of the grooves forming the array.

8. The optical detection system according to claim 7, wherein a tilt angle of the groove is steeper at the ends close to the viewing area than at the ends far away therefrom.

9. The optical detection system according to claim 1, wherein the channels of the array of transfer are deposited on a substrate.

10. The optical detection system according to claim 9, wherein a groove is provided in the substrate so as to form a channel for the circulation of a fluid carrying the particles to be detected.

11. The optical detection system according to claim 10, wherein the channels of the transfer array are buried, these channels extending under the viewing area to form a network of parallel channels, the distance between two adjacent parallel channels being lower than the wavelength of the radiation, the channels being below the viewing area at a depth lower than the wavelength of the radiation.

12. The optical detection system according to claim 10, wherein, at the viewing area, electromechanical transducers are associated with the channels of the transfer array for the control of the particle flow with respect to fluid flow lines.

13. The optical detection system according to claim 1, wherein the optical decoupler includes networks extractors located at the ends of the channels far away from the viewing area.

14. The optical detection system according to claim 13, wherein the networks extractors including a modulation of the width of the ends of the transfer array at the scale of the wavelength.

15. The optical detection system according to claim 1, wherein the decoupler includes network extractors located at the high index dielectric wires arranged at the ends of the channels far away from the viewing area and arranged in the extension of said channels.

16. The optical detection system according to claim 15, wherein the network extractors include a modulation of the width or of the section of the dielectric wires.

17. The optical detection system according to claim 15, wherein the network extractors include two piercing holes in all or part of the central dielectric wires.

18. The optical detection system according to claim 13, wherein the network extractors include a modulation of the width of the ends of the transfer array at the scale of the wavelength.

19. The optical detection system according to claim 1, comprising an illumination means and a second assembly of metal channels arranged in a single plane, one end of which is significantly closer to the viewing area, and arranged so that said second assembly forms a second array for optical information transfer around the viewing area, symmetrically relative to the first transfer array with respect to the viewing area.

20. The optical detection system according to claim 19, comprising optical coupling means between the ends far away from the viewing area and the illumination means.

21. The optical detection system according to claim 1, comprising an illumination means and a second assembly of metal channels arranged so that said second assembly forms a second optical information transfer array, symmetrically relative to the first transfer array with regard to the viewing area, the first and the second assemblies being buried under the viewing area at a depth lower than the wavelength, the first and the second assemblies being connected to each other by a network of parallel channels separated from each other by a distance lower than the radiation wavelength.

22. The optical detection system according to claim 19, wherein the illumination means works in integrated optics and is located in the plane of the second transfer array.

23. The optical detection system according to claim 19, wherein the optical coupling means include networks couplers located at the ends far away from the viewing area.

24. The optical detection system according to claim 23, wherein the networks couplers include a modulation of the width of the ends of the transfer array at the scale of the wavelength.

25. The optical detection system according to claim 19, wherein the optical coupling means include network couplers located at high index dielectric wires arranged at the end of the channels far away from the viewing area and in the extension of said channels.

26. The optical detection system according to claim 25, wherein the network couplers include a modulation of the width or of the section of the dielectric wires.

27. The optical detection system according to claim 25, wherein the network couplers include piercing holes in all or part of the central dielectric wires.

28. The optical detection system according to claim 1, comprising an illumination source directly illuminating the viewing area and a second assembly of metal channels arranged to form a second array of optical information transfer around the viewing area.

29. The optical detection system according to claim 1, comprising a plurality of arrays parallel to a single plane and located at different heights with respect to the viewing area.

30. The optical detection system according to claim 29, wherein the heights and the geometric characteristics of the arrays are determined so as to introduce a chromatism depending on that of the optic detector.

31. The optical detection system according to claim 1, comprising means for compensating the aberration of the image reconstructed by the optical detector.

32. The optical detection system according to claim 1, wherein at least one channel has a section at its end closest to said viewing area for impedance matching of the optical information from said viewing area.

33. The optical detection system according to claim 1, wherein at least one array of optical information transfer is provided with electrical contacts for the control of the electrostatic potential and the attraction or the repulsion of particles in the viewing area.

34. The optical detection system according to claim 1, wherein at least one array of optical information transfer is provided with electrical contacts for the control of electrochemical reactions in the viewing area.

35. Equipment for optical detection of particles a plurality of basic particle optical detection systems arranged on a single substrate, each of said systems further comprising an optical detector, and an assembly of metal plasmonic channels arranged in a single plane of which one end is proximate to the viewing area to allow optical information resulting from the illumination of the particles arranged in the viewing area to be transferred from one end to the other of said channels, said channels being arranged so that said assembly forms around the viewing area an array for transferring said optical information, the value of at least one spatial characteristic of said array being lower than said wavelength at the ends of said channels proximate to said viewing area, the value of at least one spatial characteristic of said array space being higher than said wavelength at the ends of said channels distant from said viewing area, said system further comprising an optical decoupler between said ends distant from said viewing area and said optical detector, the optical decoupler configured to decouple the optical information being transferred to the ends of said channels distant from said viewing area to usable light for imaging, the usable light for imaging being collected by the optical detector in order to perform the optical detection of the particles being arranged in the viewing area.

36. The optical detection equipment according to claim 35, in which the basic systems form a network in the plane of the substrate.

37. The optical detection equipment according to claim 36, further comprising at least one fluid circuit attaching at least two of said basic optical detection systems to one another.

38. The optical detection equipment according to claim 35, wherein at least two of said basic systems make up arms of an interferometric device, the viewing areas associated with each of said at least two basic systems being substantially close to each other.

39. The optical detection equipment according to claim 35, comprising means for real-time analysis of the optical signals collected by the optical detector in far-field and deduction of detected movements in the viewing area.

40. A method for manufacturing a system for optical detection of particles, comprising a step for performing a lithography on a metal layer deposited on a substrate, for the formation of plasmonic metal channels on the same plane of said substrate so that one end is proximate to a viewing area which may be illuminated by a radiation having a predetermined wavelength, during said lithography step, said metal plasmonic channels are arranged so that said assembly forms around the viewing area an optical information transfer array to transfer optical information between the ends of said plasmonic channels, the value of at least one spatial characteristic of said array being lower than said wavelength at the ends of said channels proximate to said viewing area, the value of at least one spatial characteristic of said array being higher than said wavelength at the ends of said channels distant from said viewing area, and arranging an optical decoupler between said ends distant from said viewing area and an optical detector, the optical decoupler configured to decouple the optical information being transferred to the ends of said channels distant from said viewing area to usable light for imaging, the usable light for imaging being collected by the optical detector in order to perform the optical detection of the particles being arranged in the viewing area.

41. A method for manufacturing a device for optical detection of particles, the method comprising arranging, on a single substrate, a plurality of basic systems for optical detection of particles obtained by a manufacturing method according to claim 40.

42. The manufacturing method according to the preceding claim 41, comprising a step of performing a lithography on a substrate for providing at least one groove so as to form at least one fluid channel joining each of at least two of the optical detection basic systems.

* * * * *